US009662371B2

(12) United States Patent
Hollander

(10) Patent No.: US 9,662,371 B2
(45) Date of Patent: May 30, 2017

(54) TREATMENT OF AUTISM AND SIMILAR DISORDERS

(75) Inventor: Eric Hollander, Mamoroneck, NY (US)

(73) Assignee: Neuropharmacology Services, LLC, Mamaroneck, NY (US)

( * ) Notice: Subject to any disclaimer, the term of this patent is extended or adjusted under 35 U.S.C. 154(b) by 1351 days.

(21) Appl. No.: 10/530,246

(22) PCT Filed: Oct. 3, 2003

(86) PCT No.: PCT/US03/31493
§ 371 (c)(1),
(2), (4) Date: Aug. 8, 2005

(87) PCT Pub. No.: WO2004/030524
PCT Pub. Date: Apr. 15, 2004

(65) Prior Publication Data
US 2006/0105939 A1    May 18, 2006

Related U.S. Application Data

(60) Provisional application No. 60/415,837, filed on Oct. 3, 2002.

(51) Int. Cl.
*A61K 38/11*    (2006.01)
(52) U.S. Cl.
CPC .................................... *A61K 38/11* (2013.01)
(58) Field of Classification Search
CPC ....................................................... A61K 38/11
See application file for complete search history.

(56) References Cited

U.S. PATENT DOCUMENTS

| 6,187,756 | B1 |   | 2/2001 | Lee et al. |
|---|---|---|---|---|
| 6,673,790 | B1 | * | 1/2004 | Foulon .................. C07D 209/34 514/217.03 |
| 6,894,026 | B1 | * | 5/2005 | Quay ................................ 514/9 |
| 2003/0166600 | A1 | * | 9/2003 | Ramakrishnan ..... C07K 14/723 514/44 A |
| 2007/0032410 | A1 | * | 2/2007 | Quay ................... A61K 9/0043 514/183 |

FOREIGN PATENT DOCUMENTS

| DE | 4229880 | * | 3/1994 |
|---|---|---|---|
| EP | 1556068 B1 |   | 4/2004 |
| WO | WO 00/02911 |   | 1/2000 |
| WO | WO01/74775 | * | 10/2001 |
| WO | WO 01/76629 A1 |   | 10/2001 |
| WO | WO 01/85959 |   | 11/2001 |

OTHER PUBLICATIONS

Begley et al. (Newsweek, vol. 127, Issue 20, p. 70, May 13, 1996.*
Chemical analogs (structural and functional). Wikipedia entries, accessed May 21, 2010.*
The Merck Manual Online Medical Library: anxiety (phobic) disorders. Accessed May 21, 2010.*
Panksepp J. Commentary on the possible role of oxytocin in autism. Journal of Autism and Developmental Disorders 23(3), 567-569 (1993).*
Oxytocin-deprived mice lack social memory. Autism Res. Rev. Intl. 15(1), p. 4 (2001).*
Oxytocin reduces repetitive behaviors in autistic adults. Autism Res. Rev. Intl. 16(4), p. 5 (2002).*
Insel et al., "Oxytocin, vasopressin, and autism: is there a connection?" *Biol Psychiatry* 45(2):145-157 (1999).
Lord, C. et al., "Autism Diagnostic Interview—Revised: a revised version of a diagnostic interview for caregivers of individuals with possible pervasive developmental disorders," *J Autism Dev Disord*, Oct. 24, 1994 (5): 659-685.
Eds. Baulieu, E.-E. et al., *Hormones: From Molecules to Diseases*, Hermann Publishers; 1990, pp. 283-284.
Modahl, Charlotte et al., Plasma Oxytocin Levels in Autistic Children, Society of Biological Psychiatry, 1998, pp. 270-277, vol. 43.
Parker, Karen et al., Oxytocin Biology and the Social Deficits of Autism Spectrum Disorders, Simons Foundation Autism Research Initiative, 2014.
Merriam-Webster definition of coadministration.
Medical-dictionary.thefreedictionary.com definition of coadministration.
Wiktionary definition of coadministration.

* cited by examiner

*Primary Examiner* — Jeffrey S Lundgren
*Assistant Examiner* — Sara E Townsley
(74) *Attorney, Agent, or Firm* — Tannenbaum Helpern Syracuse & Hirschtritt LLP; Gerard F. Diebner

(57) ABSTRACT

Methods of treating certain behavioral characteristics associated with autism are provided. Additionally, methods of treating disorders associated with repetitive behaviors, social deficits and/or cognitive deficits are also provided. A therapeutic amount of oxytocin or oxytocin analogs, either alone or in combination, are administered to individuals demonstrating behavioral characteristics associated with autism or other disorders to reduce the severity of the debilitating behavior. In various aspects, characteristics such as deficit in social awareness or cognitive skills and repetitive behaviors are treated. Co-administration of oxytocin and/or oxytocin analogs with known psychopharmacologic agents is also provided. Advantageously, oxytocin and oxytocin analogs do not have deleterious effects with other drugs such that administration results in few side effects.

4 Claims, 2 Drawing Sheets

TREATMENT OF AUTISM AND SIMILAR DISORDERS

CROSS REFERENCE TO RELATED APPLICATION

This application claims priority from U.S. Provisional Patent Application No. 60/415,837 filed Oct. 3, 2002 entitled, "Treatment of Autism with Oxytocin," which application is hereby incorporated by this reference in its entirety.

FIELD OF THE INVENTION

This invention relates generally to methods of treating autism and any disorder associated with repetitive behaviors, social deficits and/or cognitive deficits.

BACKGROUND OF THE INVENTION

Autism is a neurodevelopmental disorder characterized by dysfunction in three core behavioral dimensions: repetitive behaviors, social deficits, and cognitive deficits. The repetitive behavior domain involves compulsive behaviors, unusual attachments to objects, rigid adherence to routines or rituals, and repetitive motor mannerisms such as stereotypies and self-stimulatory behaviors. The social deficit dimension involves deficits in reciprocal social interactions, lack of eye contact, diminished ability to carry on conversation, and impaired daily interaction skills. The cognitive deficits can include language abnormalities.

Autism, outside of its debilitating effect on afflicted individuals, has become an increasing social burden. It is estimated that some 500,000 to 1,500,000 people in the U.S. today have autism or some form of related pervasive developmental disorder. The high incidence rate makes autism one of the most common developmental disabilities. California has found an alarming increase in the number of requests for services for autistic children. The number of requests for treatment between 1987 and 1998 has increased 273%. In addition, the US Department of Education has reported a 556% increase in the number of autistic children in the years from 1991 to 1997.

In addition to autism, many other types of disorders include similar behavioral characteristics. Such disorders include Obsessive-Compulsive Disorder (OCD), various types of eating disorders, Tourette's Syndrome, Alzheimer's Disease and Down's Syndrome, for example. Individuals suffering from these disorders further tax the educational and health care systems and are without significant pharmacological options.

Oxytocin was one of the first peptide hormones to be isolated and sequenced. It is a nonapeptide with two cysteine residues that form a disulfide bridge between positions 1 and 6 (eds. Baulieu, E.-E. and Kelly, P. A. *Hormones: From Molecules to Diseases*, Hermann Publishers; 1990, 283). It is an extremely short-lived, fast acting hormone, made by the hypothalamus of the brain, stored in the posterior pituitary, and released into the blood as needed. It stimulates certain smooth muscle cells, constricts certain blood vessels, and facilitates the sensitivity of some tissues to other hormones and nerves. The main tissues affected are: uterus, including endometrium and myometrium, vaginal, breast (both sexes), erectile (both sexes), and seminal vesicles. Oxytocin has special effects on uterine muscle contractions in both birth and orgasm, the vascular constriction that lessens placental separation bleeding, and the let-down reflex that nursing mothers have when babies cry.

Oxytocin is currently indicated for stimulation of uterine contraction to induce labor, for the control of postpartum hemorrhage following delivery of the placenta and for stimulation of lactation for breast-feeding. Oxytocin is currently prepared synthetically and sold under various trade names including Pitocin® (Parke-Davis, Morris Plains, N.J.) and Syntocinon® (Novartis Pharmaceuticals, East Hanover, N.J.).

It has recently been suggested the peptides oxytocin and vasopressin may potentially contribute to the development of the repetitive behaviors found in autism spectrum disorder patients. The theory that deficiencies in the neural pathways for oxytocin could account for many aspects of autism including its early onset and predominance in boys and the manifestation of repetitive behaviors, cognitive deficits, alterations in neural development, and genetic loading has been proposed by several researchers.

When this theory was actually evaluated by measuring oxytocin levels in the plasma of autistic children, higher levels of oxytocin were found to correlate with lower interaction and daily living skills, as well as with an overall greater deficit in social awareness.

Unfortunately, there are currently few treatment options for children and adults suffering from autism or disorders with similar behavioral characteristics. An effective therapeutic is needed to help the growing number of children and adults living with these disorders and it would be advantageous to present a relatively simple treatment capable of reducing the detrimental behaviors associated with all of them.

SUMMARY OF THE INVENTION

The present invention is directed to the administration of oxytocin, oxytocin analogs and/or combinations thereof to reduce the severity of behaviors and traits associated with autism spectrum disorder. Additionally, the present invention is directed to the administration of oxytocin, oxytocin analogs or combinations thereof to individuals suffering from any disorder that includes repetitive behaviors, social deficits, cognitive deficits, a need to know, a need to order, a need to tell, a need to ask, a self-injurious behavior and a need to touch. The reduction of the severity of behaviors associated with autism upon administration of oxytocin appears unexpected in light of earlier work, which apparently indicated that, while lower levels of oxytocin were present in autistic children when compared to normal patients, among the autistic children, higher levels of oxytocin were correlated with lower interaction and daily living skills, as well as with an overall greater deficit in social awareness. However, the present method, supported by the disclosed data, appears to alleviate symptoms and traits characteristic of autism by elevating oxytocin levels in autistic patients to levels similar to those of unafflicted individuals. The present invention provides a therapeutic method to treat individuals demonstrating autism spectrum disorder or any disorder that includes repetitive behaviors, social deficits, cognitive deficits, a need to know, a need to order, a need to tell, a need to ask, a self-injurious behavior and/or a need to touch by administering oxytocin, oxytocin analogs or combinations thereof, either alone or in combination with known psychopharmacologic agents, to reduce the severity of the behavioral characteristics associated with the disorder.

In accordance with a broad aspect of the invention a therapeutic amount of an oxytocin selected from the group consisting essentially of oxytocin, oxytocin analogs and combinations thereof is effective in treating individuals demonstrating autism spectrum disorder or any disorder that includes repetitive behaviors, social deficits, cognitive deficits, a need to know, a need to order, a need to tell, a need to ask, a self-injurious behavior and a need to touch. In accordance with the present invention, administration of a therapeutic amount of oxytocin, an oxytocin analog or combination thereof is effective in reducing behavioral characteristics associated with any of these disorders. In a particular embodiment, repetitive behavioral characteristics are reduced by the administration of an effective amount of oxytocin, oxytocin analogs, or combination thereof. In another particular embodiment, social awareness deficiencies are improved by the administration of an effective amount of oxytocin, oxytocin analogs, or combination thereof. In still another particular embodiment, cognitive deficits are improved by the administration of an effective amount of oxytocin, oxytocin analogs, or combination thereof.

In accordance with the present invention, a therapeutic amount of an oxytocin selected from the group consisting essentially of oxytocin, oxytocin analogs and combinations thereof is co-administered with psychopharmacologic agents to treat individuals demonstrating autism spectrum disorder or any disorder that includes repetitive behaviors, social deficits, cognitive deficits, a need to know, a need to order, a need to tell, a need to ask, a self-injurious behavior and/or a need to touch. The psychopharmacologic agents, which are useful, are, for example, antipsychotics, tranquilizers, sedatives, antidepressants, anticonvulsants, and the like. In particular embodiments, such psychopharmacologic agents specifically affect the opiate, noradrenergic, dopaminergic, serotonergic, glutamattergic and GABAergic systems, for example. In another particular embodiment, such psychopharmacologic agent is capable of effecting gene transcription, specifically in genes responsible for brain development.

Oxytocin analogs useful in accordance with the instant invention are those compounds, moieties and/or fragments, which demonstrate bioactivity similar to or greater than oxytocin. Examples include, 4-threonine-1-hydroxy-deaminooxytocin, 9-deamidooxytocin, 7-D-proline-oxytocin and its deamino analog, (2,4-diisoleucine)-oxytocin, deamino oxytocin analog, 1-deamino-1-monocarba-E 12-[Tyr(OMe)]-OT(dCOMOT), carbetocin, [Thr4-Gly7]-oxytocin, oxypressin, deamino-6-carba-oxytoxin, and the like. Additional examples include (dC60), d[Lys(8)(5/6C-Flu)]VT, d[Thr(4), Lys(8)(5/6C-Flu)]VT, [HO(1)][Lys(8)(5/6C-Flu)]VT, [HO(1)][Thr(4), Lys(8)(5/6C-Flu)]VT, d[Om(8)(5/6C-Flu)]VT, d[Thr(4), Om(8)(5/6C-Flu)]VT, [HO(1)][Om(8)(5/6C-Flu)]VT, [HO(1)][Thr(4), Om(8)(5/6C-Flu)]VT and the like, where Flu means fluorescein.

Disorders including repetitive behaviors that may be treated with the methods of the present invention include Obsessive-Compulsive Disorder (OCD); eating disorders, such as bulimia, anorexia nervosa and Binge Eating Disorder; Body Dysmorphic Disorder, trichotillomania; hypochondriasis; Tourette's Syndrome; Depersonalization Disorder; Impulse Control Disorder, Pathological Gambling; Internet Addiction Pyromania; Compulsive Shopping; Compulsive Sexual Behaviors, such as paraphilias, nonparaphilia and sexual addiction; kleptomania; Intermittent Explosive Disorder, self-injurious behaviors; Sydenham's Chorea Torticollis Stereotypic Disorders, and the like.

Disorders including social deficits that may be treated with the methods of the present invention can be selected from the group consisting essentially of Social Anxiety Disorder; personality disorders, such as Schizoid Personality Disorder, Schizotypal Personality Disorder and Borderline Personality Disorder, attachment disorders, attachment disorders secondary to early trauma, abuse or neglect and the like.

Disorders including cognitive deficits that may be treated with the methods of the present invention include Alzheimer's Disease, Jacob Creutzfeld's Disease, Down's Syndrome, Mild Cognitive Decline, Attention Deficit Disorder (ADD), Attention Deficit Hyperactivity Disorder, and the like.

A particular embodiment of the present invention includes a method of treating an individual with autism with a 25 ug/ml oxytocin solution intravenously for four hours. During the four hours the solution is to be titrated every 15 minutes of the first hour by 25 ml, every 15 minutes of the second hour by 50 mL, every 15 minutes of the third hour by 100 mL with delivery to remain constant the fourth hour.

Another particular embodiment of the present invention includes a method of treating an individual with a disorder including repetitive behaviors, social deficits and/or cognitive deficits with a 25 ug/ml oxytocin solution intravenously for four hours. During the four hours the solution is to be titrated every 15 minutes of the first hour by 25 ml, every 15 minutes of the second hour by 50 mL, every 15 minutes of the third hour by 100 mL with delivery to remain constant the fourth hour.

BRIEF DESCRIPTION OF THE DRAWINGS

The following drawings form part of the present specification and are included to further demonstrate certain embodiments. These embodiments may be better understood by reference to one or more of these drawings in combination with the detailed description of specific embodiments presented herein.

DESCRIPTION OF ILLUSTRATIVE EMBODIMENTS

Definitions

Figure 1:
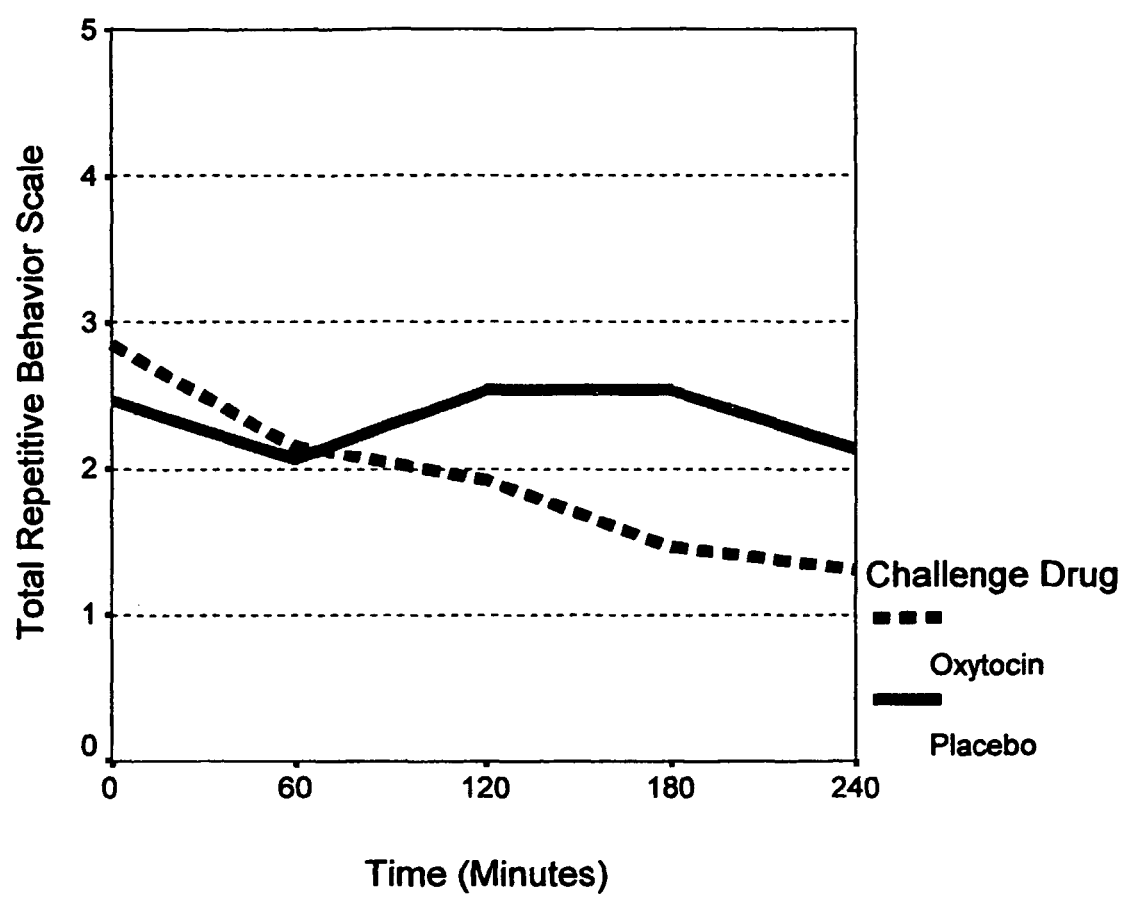
FIG. 1 illustrates the effects of an infusion of oxytocin or placebo on repetitive behaviors in autism spectrum disorder patients over time in accordance with a particular method of the present invention. The average total repetitive behavioral score of the subjects was recorded between 0 and 240 minutes after administration of either oxytocin (dashed) or placebo (solid).

For the purposes of the present invention, the following terms shall have the following meanings:

The term "oxytocin" refers to oxytocin, oxytocin analogs and combinations thereof. The term "analog" or "agonist" refers to any molecule that demonstrates oxytocin activity. Such molecule may be a synthetic analog, fragment of oxytocin, pharmaceutically acceptable salt of oxytocin, or endogenous biological molecule other than oxytocin capable of oxytocin-like activity. In sum, an oxytocin analog refers to any molecule that demonstrates bioactivity less than, similar to or greater than oxytocin itself.

The term "autism" refers to an individual demonstrating any one or all of the symptoms and characteristics associated with autism. Such individual may fit particular diagnostic criteria, such as Autistic Disorder, Asperger's Disorder, Atypical Autism or Pervasive Developmental Disorder, NOS (not otherwise specified), Rett's Disorder or Childhood Disintegrative Disorder, or the broader autism phenotype disorder or such individual may not fit a discrete diagnostic category at all. Due to the many presentations of the disease called autism, the present invention will use the term "autism" to refer to all of the above disorders.

Moreover, for the purposes of the present invention, the term "a" or "an" entity refers to one or more of that entity; for example, "a protein" or "an oxytocin molecule" refers to one or more of those compounds or at least one compound. As such, the terms "a" or "an", "one or more" and "at least one" can be used interchangeably herein. It is also to be noted that the terms "comprising," "including," and "having" can be used interchangeably.

Furthermore, a compound "selected from the group consisting of" refers to one or more of the compounds in the list that follows, including mixtures (i.e. combinations) of two or more of the compounds. According to the present invention, an isolated or biologically pure oxytocin is a compound that has been removed from its natural milieu. As such, "isolated" and "biologically pure" do not necessarily reflect the extent to which the compound has been purified. An isolated compound of the present invention can be obtained from its natural source, can be produced using molecular biology techniques or can be produced by chemical synthesis.

Oxytocin Analogs

In certain embodiments, oxytocin analogs are utilized. Examples of particular oxytocin analogs for use with the methods of the present invention include 4-threonine-1-hydroxy-deaminooxytocin, 9-deamidooxytocin, an analog of oxytocin containing a glycine residue in place of the glycinamide residue; 7-D-proline-oxytocin and its deamino analog; (2,4-diisoleucine)-oxytocin, an analog of oxytocin with natriuretic and diuretic activities; deamino oxytocin analog; a long-acting oxytocin (OT) analog, 1-deamino-1-monocarba-E12-[Tyr(OMe)]-OT(dCOMOT); carbetocin, a long-acting oxytocin analog; oxytocin analog [Thr4-Gly7]-oxytocin (TG-OT); oxypressin, an equipotent analog of oxytocin and vasopressin; Ile-conopressin; atosiban; deamino-6-carba-oxytoxin (dC60), a potent oxytocin analog considered to be resistant to some of the physiologically significant enzymatic systems; and the like. Additionally, oxytocin analogs may also include d[Lys(8)(5/6C-Flu)]VT, d[Thr(4), Lys(8)(5/6C-Flu)]VT, [HO(1)][Lys(8)(5/6C-Flu)]VT, [HO(1)][Thr(4), Lys(8)(5/6C-Flu)]VT, d[Orn(8)(5/6C-Flu)]VT, d[Thr(4), Orn(8)(5/6C-Flu)]VT, [HO(1)][Orn(8)(5/6C-Flu)]VT, [HO(1)][Thr(4), Orn(8)(5/6C-Flu)]VT and, the like, where flu is fluorescein.

In another particular embodiment, the oxytocin analog is an oxytocin fragment. Such fragment may be chemically synthesized or derived by any known means. Oxytocin fragments of the present invention retain bioactivity less than, similar to or greater than oxytocin. Such fragments may be capable of crossing the blood brain barrier.

In another embodiment, the oxytocin analog is a synthetic oxytocin molecule that equals or exceeds oxytocin in bioactivity. Such analog molecule is capable of acting in a manner similar to endogenous oxytocin, including binding the oxytocin receptor. Analogs of this type may be derivatives of oxytocin or have completely new molecular structures.

The skilled artisan will realize that the compounds listed above are exemplary only and that many variations may be used, depending on the particular oxytocin analog utilized, and the desired physiological effect. Such variations are known in the art.

Treatment of Autism

Autism impacts the normal development of the brain in the areas of social interaction and communication skills. Children and adults with autism typically have difficulties in verbal and non-verbal communication, social interactions, and leisure or play activities. The disorder makes it hard for them to communicate with others and relate to the outside world. In some cases, aggressive and/or self-injurious behavior may be present. Persons with autism may exhibit repeated body movements (hand flapping, rocking), unusual responses to people or attachments to objects and resistance to changes in routines. Individuals may also experience sensitivities in the five senses of sight, hearing, touch, smell, and taste.

Autism is a spectrum disorder and the symptoms and characteristics of autism can present themselves in a wide variety of combinations and range from mild to severe in intensity. Although autism is defined by a certain set of behaviors, children and adults can exhibit a wide variety of combinations of the behaviors with many different levels of severity. In other words, two children, both with the same diagnosis, can act very differently from one another and have varying skill sets. Therefore, there is no standard autistic patient. The medical profession has attempted to create several categories of autism based on diagnostic criteria. A standard category is Autistic Disorder, which is displayed by individuals with impairments in social interaction, communication, and imaginative play prior to 3 years of age and is categorized by stereotyped behaviors, interests and activities. A second category is Asperger's disorder, which is characterized by impairments in social interactions and the presence of restricted interests and activities. Children or adults with Asperger's disorder generally show no clinically significant delay in language and have average to above average intelligence. A third category, Atypical Autism or Pervasive Developmental Disorder, is a diagnosis that is made when a child does not meet the criteria for a specific diagnosis but demonstrates severe and pervasive impairment in specified behaviors.

Rett's Disorder is a progressive disorder only observed in females. This disease is categorized by a period of normal development and then a loss of previously acquired skills, loss of the purposeful use of the hands and replacement of such normal hand movement with extreme repetitive hand movements. Such disease usually begins between the ages of one and four. A similar disorder that strikes both genders is called Childhood Disintegrative Disorder and it is characterized by normal development for at least the first 2 years of life and loss of previously acquired skills shortly thereafter. Additionally, abnormally high rates of all types of autism are found in children delivered to mothers who were induced with oxytocin or an oxytocin analog, such as pitocin.

In addition, some individuals with autism may also have other disorders which affect the functioning of the brain such as: Epilepsy, Mental Retardation, Down Syndrome, or genetic disorders such as: Fragile X Syndrome, Landau-Kleffner Syndrome, William's Syndrome, obsessive-compulsive disorder, attention deficit hyperactivity disorder or Tourette's Syndrome, for example. Autistic individuals with additional disorders may be treated by the methods of the present invention.

In the medical sense, there is no cure for the differences in the brain, which result in autism. Current therapies include adaptive physical education, occupation therapy, special education and speech therapy. Vocational training is also recommended from an early age to begin to teach autistic children daily living skills.

There are also a wide variety of psychopharmacologic agents, including sedatives, tranquilizers, antipsychotics, antidepressants and anticonvulsants available to alleviate the symptoms associated with autism. Many of these pharmaceuticals have serious side effects and need to be carefully monitored. In addition, many interact with other medications, making administration of therapeutics a balancing act in order to prevent a toxic reaction. All current medications are incapable of replacing the need for appropriate education and behavior management.

Figure 2:
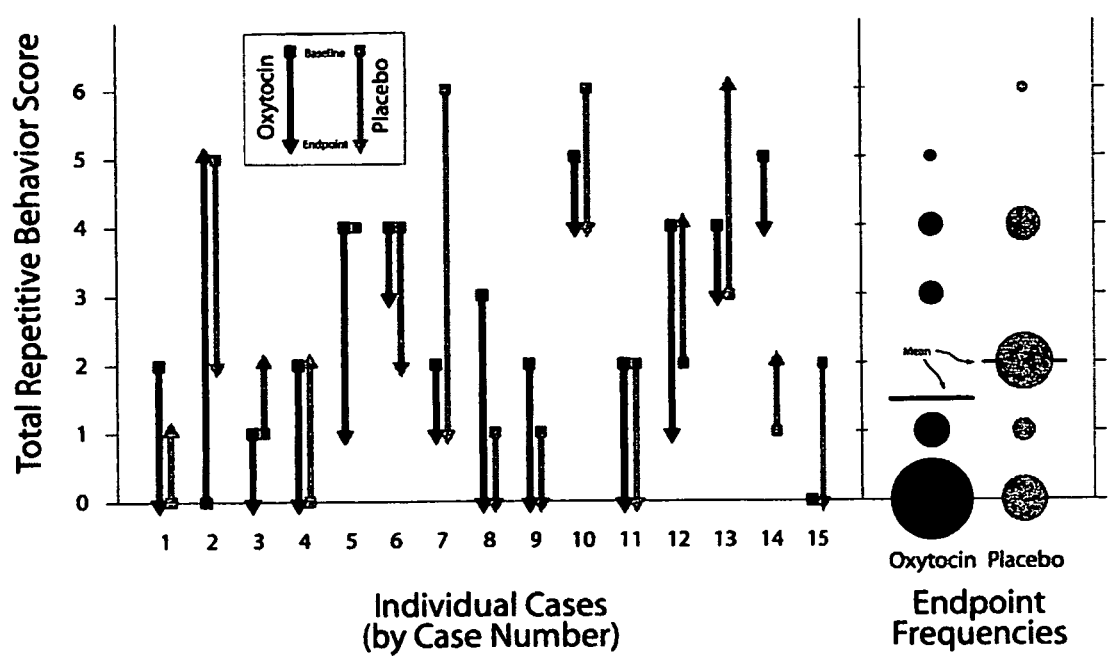
FIG. 2 illustrates the effects on each subject (1-16) of an infusion of oxytocin (black) and placebo (gray) on repetitive behaviors from baseline (0 minutes as indicated by the square) to endpoint (240 minutes as indicated by the arrow) in accordance with a particular method of the present invention.

In treating characteristics associated with autism, according to the invention, a therapeutically effective amount of oxytocin, oxytocin analogs or combinations thereof is administered to an individual demonstrating autism spectrum disorder characteristics. For example, FIG. 1 displays a particular embodiment of the present invention where the total number of repetitive behaviors observed following the administration of oxytocin to an autistic study group (dashed line) appears to decrease, whereas the administration of a placebo did not appear to decrease repetitive behaviors (solid line). Likewise, another particular embodiment is illustrated in FIG. 2 where the response of individual subjects to both oxytocin and a placebo challenge is demonstrated. Nearly all of the subjects illustrated in FIG. 2 appear to demonstrate a decrease, shown as a downward pointing black arrow, in repetitive behaviors following oxytocin treatment. The horizontal lines at the far right-hand side of the graph show that the mathematical mean number of total repetitive behaviors for the oxytocin challenge appears to be lower than that for the placebo challenge.

Alternatively, any of the oxytocin treatments may precede or follow the administration of another agent by intervals ranging from minutes to weeks. In embodiments where the other agent and any of the oxytocin or oxytocin analogs are administered separately, one would generally ensure that a significant period of time did not expire between the time of each delivery, such that the agent and oxytocin or oxytocin analog would still be able to exert an advantageously combined (e.g., synergistic) effect on the patient. In such instances, it is contemplated that one would administer the two therapeutics within about 12-24 hours of each other, and, more preferably, within about 6-12 hours of each other, with a delay time of only about 12 hours being most preferred. In some situations, it may be desirable to extend the duration of treatment with just the therapeutic agent, for example, where several days (2,3,4,5,6, or 7) to several weeks (1,2,3,4,5,6, 7 or 8) lapse between the respective administrations.

Agents suitable for use in combination therapy are any chemical compound or treatment method useful to patients with autism. Such agents and factors include sedatives, tranquilizers, antipsychotics, antidepressants or anticonvulsants. Agents may additionally include those capable of affecting the opiate, noradrenergic, dopaminergic, serotonergic, glutamatergic, and/or GABAergic systems. Agents may further affect gene transcription, specifically in genes responsible for brain development. This may be particularly useful in children delivered to mothers who had their labor induced by oxytocin or an oxytocin analog, as administration of oxytocin while in-utero may lead to later abnormal brain development. Later administration of oxytocin may lessen or prevent the effect of such oxytocin administration or lessen the behavioral characteristics associated with autism if it later develops in the child.

Treatment of Other Types of Disorders

Individuals suffering from disorders that include behaviors similar to those observed in autistic patients may be treated by the methods of the present invention. Such disorders may be associated with repetitive behaviors, social deficits and/or cognitive deficits and can also be treated with the methods of the present invention.

Disorders associated with repetitive behaviors include Obsessive-Compulsive Disorder (OCD); eating disorders, such as bulimia, anorexia nervosa and Binge Eating Disorder; Body Dysmorphic Disorder; trichotillomania; hypochondriasis; Tourette's Syndrome; Depersonalization Disorder; Impulse Control Disorder, Pathological Gambling; Internet Addiction Pyromania; Compulsive Shopping; Compulsive Sexual Behaviors, such as paraphilias, nonparaphilia and sexual addiction; kleptomania; Intermittent Explosive Disorder; self-injurious behaviors; Sydenham's Chorea Torticollis Stereotypic Disorders, and the like.

Disorders associated with social deficits include Social Anxiety Disorder; personality disorders, such as Schizoid Personality Disorder, Schizotypal Personality Disorder and Borderline Personality Disorder; attachment disorders, attachment disorders secondary to early trauma, abuse or neglect and the like.

Disorders associated with cognitive deficits include Alzheimer's Disease, Jacob Creutzfeld's Disease, Down's Syndrome, Mild Cognitive Decline, Attention Deficit Disorder (ADD), Attention Deficit Hyperactivity Disorder, and the like.

In treating characteristics associated with these various disorders, a therapeutically effective amount of oxytocin, oxytocin analogs or combinations thereof is administered to an individual demonstrating a repetitive behavior, a social deficit and/or a cognitive deficit.

Alternatively, any of the oxytocin treatments may be co-administered, precede or follow the administration of another agent by intervals ranging from minutes to weeks. In embodiments where the other agent and any of the oxytocin or oxytocin analogs are administered separately, one would generally ensure that a significant period of time did not expire between the time of each delivery, such that the agent and oxytocin or oxytocin analog would still be able to exert an advantageously combined (e.g., synergistic) effect on the patient. In such instances, it is contemplated that one would administer the two therapeutics within about 12-24 hours of each other, and, more preferably, within about 6-12 hours of each other, with a delay time of only about 12 hours being most preferred. In some situations, it may be desirable to extend the duration of treatment with just the therapeutic agent, for example, where several days (2,3,4,5,6, or 7) to several weeks (1,2,3,4,5,6, 7 or 8) lapse between the respective administrations.

Agents suitable for use in combination therapy are any chemical compound or treatment method useful to patients with disorders associated with repetitive behaviors, social deficits and cognitive deficits. Such agents and factors include sedatives, tranquilizers, antipsychotics, antidepressants, anticonvulsants, and the like. Agents may additionally include those capable of affecting the opiate, noradrenergic, dopaminergic, serotonergic, glutamatergic, and/or GABAergic systems. Agents may further affect gene transcription, specifically in genes responsible for brain development.

Pharmaceutical Compositions and Routes of Administration

An aqueous solution of a therapeutically effective amount of oxytocin or oxytocin analogs, dissolved or dispersed in a pharmaceutically acceptable carrier or aqueous medium can be administered to an individual in order to treat behavioral characteristics associated with autism. The phrases "pharmaceutically or pharmacologically acceptable" refer to molecular entities and compositions that do not produce an unacceptably frequent adverse, allergic or other untoward reaction when administered to an animal, or a human, as appropriate. Additionally, the term "therapeutically effective dose" or "therapeutic dose" refers to the administration of a quantity that renders a therapeutic, rather than an adverse, allergic or other untoward reaction when administered to an individual, such as an animal, or human.

Aqueous solutions to be administered in accordance with the methods of the present invention comprise an effective amount of the compound, dissolved or dispersed in a pharmaceutically acceptable carrier or aqueous medium. Such compositions can also be referred to as inocula. As used herein, "pharmaceutically acceptable carrier" includes any and all solvents, dispersion media, coatings, antibacterial and antifungal agents, isotonic and absorption delaying agents and the like. The use of such media and agents for pharmaceutically active substances is well known in the art. Except insofar as any conventional media or agent is incompatible with the active ingredient, its use in the therapeutic compositions is contemplated. Supplementary active ingredients can also be incorporated into the compositions. For human administration, preparations should meet sterility, pyrogenicity, general safety and purity standards as required by FDA and other regulatory agency standards.

The active oxytocin or oxytocin analog compounds will generally be formulated for parenteral administration, e.g., formulated for injection via the intravenous, intramuscular, subcutaneous, or intraperitoneal routes. The preparation of an aqueous composition that contains an active component or ingredient will be known to those of skill in the art in light of the present disclosure. Typically, such compositions can be prepared as injectables, either as liquid solutions or suspensions; solid forms suitable for use in preparing solutions or suspensions upon the addition of a liquid prior to injection can also be prepared; and the preparations can also be emulsified.

The pharmaceutical forms suitable for injectable use include sterile aqueous solutions or dispersions; formulations including sesame oil, peanut oil or aqueous propylene glycol; and sterile powders for the extemporaneous preparation of sterile injectable solutions or dispersions. In cases of injectable use, the form must be sterile and fluid. It must also be stable under the conditions of manufacture and storage and must be preserved against the contaminating action of microorganisms, such as bacteria and fungi.

Solutions of the active oxytocin or oxytocin analog compounds effective in accordance with the method of the instant invention can be prepared in water suitably mixed with a surfactant, such as hydroxypropylcellulose. Dispersions can also be prepared in glycerol, liquid polyethylene glycols, and mixtures thereof, and in oils. Under ordinary conditions of storage and use, these preparations contain a preservative to prevent the growth of microorganisms.

The carrier can also be a solvent or dispersion medium containing, for example, water, ethanol, polyol (for example, glycerol, propylene glycol, liquid polyethylene glycol, and the like), suitable mixtures thereof, and vegetable oils. The proper fluidity can be maintained, for example, by the use of a coating, such as lecithin, by the maintenance of the required particle size in the case of dispersion and by the use of surfactants. In the case of microparticles, an aqueous suspending medium may optionally contain a viscosity enhancer such as sodium carboxymethylcellulose and optionally a surfactant such as Tween-20. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

Sterile injectable solutions are prepared by incorporating the active compounds in the required amount in the appropriate solvent with various amounts of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof. The preparation of more, or highly, concentrated solutions for direct injection is also contemplated, where the use of DMSO as solvent is envisioned to result in extremely rapid penetration, delivering high concentrations of the active agents to a small area.

Upon formulation, solutions will be administered in a manner compatible with the dosage formulation and in such amount as is therapeutically effective. The formulations are easily administered in a variety of dosage forms, such as the type of injectable solutions described above, but time release formulations, such as drug release capsules or depot injections, and the like can also be employed.

For parenteral administration in an aqueous solution, for example, the solution should be suitably buffered if necessary and the liquid diluent first rendered isotonic with sufficient saline or glucose. These particular aqueous solutions are especially suitable for intravenous, intramuscular, subcutaneous and intraperitoneal administration. In this connection, sterile aqueous media that can be employed will be known to those of skill in the art in light of the present disclosure. For example, a unit dose could be dissolved in 1 ml of isotonic NaCl solution and either added to 1000 ml of hypodermoclysis fluid or injected at the proposed site of infusion.

The term "unit dose" refers to physically discrete units suitable for use in a subject, each unit containing a predetermined quantity of the therapeutic composition calculated to produce the desired responses, discussed above, in association with its administration, i.e., the appropriate route and treatment regimen. The quantity to be administered, both according to number of treatments and unit dose, depends on the subject to be treated, the state of the subject and the protection desired. The person responsible for administration will, in any event, determine the appropriate dose for the individual subject. Activity of oxytocin is expressed in terms of USP units, as defined in a bioassay of uterine-stimulating potency of posterior pituitary extracts. One USP unit is the equivalent of approximately 2 ug of pure peptide.

The active therapeutic agents may be formulated within a mixture to comprise about 0.0001 to 1.0 milligrams, or about 0.001 to 0.1 milligrams, or about 1.0 to 100 milligrams or even about 0.01 to 1.0 grams per dose or so. Multiple doses can also be administered.

In addition to the oxytocin or oxytocin analog compounds formulated for parenteral administration, such as intravenous, subcutaneous or intramuscular injection, other alternative methods of administration of the present invention may also be used, including but not limited to intradermal administration, pulmonary administration, buccal administration, transdermal administration and transmucosal administration. All such methods of administration are well known in the art.

One may also use intranasal administration in accordance with the present invention, such as with nasal solutions or sprays, aerosols or inhalants. Nasal solutions are usually aqueous solutions designed to be administered to the nasal passages in drops or sprays. Nasal solutions are prepared so that they are similar in many respects to nasal secretions. Thus, the aqueous nasal solutions usually are isotonic and slightly buffered to maintain a pH of 5.5 to 6.5. In addition, antimicrobial preservatives, similar to those used in ophthalmic preparations, and appropriate drug stabilizers, if required, may be included in the formulation. Various commercial nasal preparations are known and include, for example, antibiotics and antihistamines and are used for asthma prophylaxis.

In a particular embodiment, the route of administration is a route designed for optimum delivery of oxytocin, oxytocin analogs, oxytocin fragments or combinations thereof to the central nervous system.

Additional formulations, which are suitable for other modes of administration, include suppositories and pessaries. A rectal pessary or suppository may also be used. Suppositories are solid dosage forms of various weights and shapes, usually medicated, for insertion into the rectum or the urethra. After insertion, suppositories soften, melt or dissolve in the cavity fluids. For suppositories, traditional binders and carriers generally include, for example, polyalkylene glycols or triglycerides; such suppositories may be formed from mixtures containing the active ingredient in the range of 0.5% to 10%, preferably 1%-2%.

Oral formulations include such normally employed excipients as, for example, pharmaceutical grades of mannitol, lactose, starch, magnesium stearate, sodium saccharine, cellulose, magnesium carbonate and the like. These compositions take the form of solutions, suspensions, tablets, pills, capsules, sustained release formulations or powders. In certain defined embodiments, oral pharmaceutical compositions will comprise an inert diluent or assimilable edible carrier, or they may be enclosed in a hard or soft shell gelatin capsule, or they may be compressed into tablets, or they may be incorporated directly with the food of the diet. For oral therapeutic administration, the active compounds may be incorporated with excipients and used in the form of ingestible tablets, buccal tables, troches, capsules, elixirs, suspensions, syrups, wafers, and the like. Such compositions and preparations should contain at least 0.1% of active compound. The percentage of the compositions and preparations may, of course, be varied and may conveniently be between about 2 to about 75% of the weight of the unit, or preferably between 25-60%. The amount of active compounds in such therapeutically useful compositions is such that a suitable dosage will be obtained.

The tablets, troches, pills, capsules and the like may also contain the following: a binder, such as gum tragacanth, acacia, cornstarch, or gelatin; excipients, such as dicalcium phosphate; a disintegrating agent, such as corn starch, potato starch, alginic acid and the like; a lubricant, such as magnesium stearate; and a sweetening agent, such as sucrose, lactose or saccharin may be added or a flavoring agent, such as peppermint, oil of wintergreen, or cherry flavoring. When the dosage unit form is a capsule, it may contain, in addition to materials of the above type, a liquid carrier. Various other materials may be present as coatings or to otherwise modify the physical form of the dosage unit. For instance, tablets, pills, or capsules may be coated with shellac, sugar or both. Enteric formulations are often used to protect an active ingredient from the strongly acidic contents of the stomach. Such formulations are created by coating a solid dosage form with a film of a polymer which is insoluble in acidic environments, and soluble in basic environments. Exemplary films are cellulose acetate phthalate, polyvinyl acetate phthalate, hydroxypropyl methylcellulose phthalate and hydroxypropyl methylcellulose acetate succinate. A syrup of elixir may contain the active compounds sucrose as a sweetening agent, methyl and propylparabens as preservatives, a dye and flavoring, such as cherry or orange flavor.

In addition, alternative suitable compositions of the present invention may be used, including but not limited to hydrogels, vaginal ring, patches, crystals, gels, liposomes, and implants. All such compositions are well known in the art.

In a particular embodiment, the formulation is one which has long lasting activity in the central nervous system.

EXAMPLES

The following examples are included to demonstrate particular embodiments of the invention. It should be appreciated by those of skill in the art that the techniques disclosed in the examples which follow represent techniques discovered by the inventors to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

Treatment of Adults with Autistic and Asperger's Disorders with Oxytocin

Experimental Design

To evaluate the role of oxytocin in treating autism spectrum disorders, fifteen adult patients (mean age=32.9 years, range=19.4-55.6) (14 male, 1 female) diagnosed with autism (N=6) or Asperger's disorder (N=9) received oxytocin and placebo challenges during visits separated by 2-3 weeks to the General Clinical Research Center of the Department of Psychiatry, Seaver Autism Research Center at the Mount Sinai School of Medicine (New York, N.Y.). All patents were carefully evaluated and diagnosed according to both DSM-IV criteria and the Autism Diagnostic Interview-Revised (Lord C, Rutter M, LeCouteur A (1994): Autism Diagnostic Interview-Revised: a revised version of a diagnostic scale for caregivers of individuals with possible pervasive developmental disorders. *Journal of Autism and Developmental Disorders* 24:659-685.), on which the patients with autism scored within the autistic range and those with Asperger's disorder did not.

Patients and their guardians signed written informed consent agreements, and the study was carried out in accordance with the Declaration of Helsinki as adopted and promulgated by the National Institutes of Health. All patents were medically healthy, without a current or past history of schizophrenia, psychotic disorders, substance abuse, other Axis I mental disorders, or seizure disorders. Patients were of average intelligence, with a mean IQ (±SD) of 90.33 (±9.90) (range=74-110). Nine patients were medication free for greater than one year prior to the study; three patents were medication free for greater than six weeks prior to the study (one was previously on fluoxetine, one on sertraline and one on bupropion); and the remaining three patents were medication free for a minimum of two weeks prior to and throughout the study (one was previously on fluvoxamine and risperidone, one on sertraline and one on clonazepam).

Each subject served as his/her own control; a control group of individuals free of autism spectral disorder was not included because the repetitive behaviors being monitored are characteristic of autism spectrum patients but are not exhibited by individuals unafflicted by ASD. Each individual subject underwent two identical challenge days in which they received a continuous infusion over 4 hours of synthetic oxytocin (Pitocin®) or placebo.

All subjects were admitted into the General Clinical Research Center on the evening prior to each challenge. Following an overnight fast, the subject was awakened at 8:00 AM and an indwelling intravenous catheter inserted. At 8:30 AM vital signs were taken, and these continued to be monitored every half-hour. At 9:00 AM, 6 cc of blood were drawn and the oxytocin/placebo infusion was administered in a randomized double-blind fashion. The initial vial of Pitocin® (10 u/mL) combined aseptically with a 1.0 L bag of normal saline was first given at a rate of 10 mL/hr which is equivalent to a dose rate of 0.1 units/hour. The infusion was initiated at a low rate to minimize potential side effects, and the rate gradually titrated up. Specifically, the dose rate was titrated every 15 minutes by 25 mL/hour in the first hour, 50 mL/hour in the second hour, 100 mL/hour in the third hour, and held constant at the maximum rate of 700 mL/hr during the fourth hour. This created a range of dosing from 0.1 U/hour to 7 U/hour. See below:

| Time (hr) | Time (min) | infusion rate (ml/hr) | Dose rate (U/hr) |
|---|---|---|---|
| 0 | 0 | 10 | 0.1 |
| .25 | 15 | 25 | 0.25 |
| .5 | 30 | 50 | 0.5 |
| .75 | 45 | 75 | 0.75 |
| 1 | 60 | 100 | 1.0 |
| 1.25 | 75 | 150 | 1.5 |
| 1.5 | 90 | 200 | 2.0 |
| 1.75 | 105 | 250 | 2.5 |
| 2 | 120 | 300 | 3.0 |
| 2.25 | 135 | 400 | 4.0 |
| 2.5 | 150 | 500 | 5.0 |
| 2.75 | 165 | 600 | 6.0 |
| 3 | 180 | 700 | 7.0 |
| 3.25 | 195 | 700 | 7.0 |
| 3.5 | 210 | 700 | 7.0 |
| 3.75 | 225 | 700 | 7.0 |
| 4 | 240 | 700 | 7.0 |

The combined solution, rotated in an infusion bottle to insure thorough mixing, was added to the system by a constant infusion pump to accurately control the rate of infusion.

Staff members were given specific instructions to discontinue increasing the rate of infusion if the patient experienced significant side effects. In order to assess possible cardiovascular effects, blood pressure and pulse were recorded every half hour. Oral temperature was recorded every hour. All fifteen subjects returned in 2-3 weeks for an identical challenge administered with the other infusion substance.

Severity of repetitive autistic behaviors was evaluated using a method developed during past research with the autistic population. Six behaviors were assessed: need to know, repeating, ordering, need to tell/ask, self-injury, and touching. The ratings were completed at baseline (O), 60, 120, 180, and 240 minutes and reported. The frequency of each of the six repetitive behaviors was recorded using a four point ordinal scale with the following values: 0=never, 1=rarely, 2=sometimes, 3=constantly. These ratings were done following a 15 to 20 minute interview during which several other measures were administered and the rater had the opportunity to observe the patient's behavior in this domain.

The scale's validity was confirmed during another study in which 15 ratings were conducted by 3 raters using both this instrument and the YBOCS compulsion severity scale, utilizing the YBOCS symptom checklist to elicit types of repetitive behaviors. It was determined that this scale had a correlation of 0.81 with the YBOCS compulsion scale (p=0.01). There was 100% agreement between raters on the measure of repetitive behaviors when rating a patient over the same time period.

A repeated measure analysis of variance (ANOVA) was conducted looking at the two infusions (oxytocin vs. placebo) over time (0, 60, 120, 180 and 240 minutes). A logarithmic transformation was done for the repetitive behavior ratings because the data were not normally distributed. Baseline differences on the oxytocin vs. placebo days were examined using paired sample t-tests. Differences in response between patients with autism and patients with Asperger's disorder were examined using independent sample t-tests. Pearson correlations between behavioral response and physiological measures (blood pressure, pulse, and oral temperature) and chi square analysis comparing behavioral responses in patients with and without side effects were also conducted. A significance criterion of $p<0.05$ was used in all analyses.

Results

There was no significant or trend difference in baseline severity of repetitive behaviors on the oxytocin and placebo days. There was a significantly greater reduction in repetitive behaviors over time following oxytocin compared to placebo (drug×time interaction: F=3.487, df=4, 52, p=0.027), see FIG. 1. There was no significant main effect for drug (F=1.835, df=1, 13, p=0.199), but there was a significant main effect for time (F=3.239, df=4, 52, p=0.030). For the purpose of understanding possible differences between the individual dimensions of repetitive behavior, analyses of the individual items was conducted using the same ANOVA design as used for the primary analysis. There were no significant differences at $p<0.05$ for the individual dimensions on the oxytocin versus placebo infusions over time, but two items showed a directional difference ($p<0.10$); these were repeating (time×drug interaction: F=2.70, df=4, 52, p=0.086) and touching behavior (time×drug interaction: F=2.444, df=4, 52, p=0.093).

The baseline (O) and endpoint (240 minutes) ratings for each individual patient are presented in FIG. 2, showing that on the oxytocin infusion there was a decrease in repetitive behaviors for 13 patients (86.7%), an increase for 1 patient and no change for 1 patient, in contrast to ratings taken during the placebo infusion when only 6 patients (40%) showed decreased repetitive behaviors, while 6 increased, and 2 were unchanged.

Individuals who responded to oxytocin often had a decrease in the number of different types of repetitive behavior from 3 or 4 at baseline to none or one at endpoint. Thus, not only did the severity decrease over time, but so did the number of different types of repetitive behaviors on oxytocin, which was clinically meaningful. In contrast, during the placebo challenge, 6 of the participants had an increase in repetitive behaviors while only one did on oxytocin, which suggests that the structured challenge situation itself may have caused an increase in these behaviors in some patients, which was prevented by oxytocin. Patients with autism did not differ from patients with Asperger's disorder following oxytocin infusion (t=0.687, df=13, p=0.504). There were no significant effects of either infusion on blood pressure, pulse, or temperature, and these measures did not marginally or significantly correlate with the behavioral measures of response to the infusion agents. Side effects on oxytocin were mild and included drowsiness, anxiety, depression, headache, tingling, backache, trembling, restlessness, stomach cramps, and enuresis. Placebo side effects included mild drowsiness, anxiety, and headache. There was no relationship between the presence or number of side effects and behavioral response to oxytocin or placebo.

Example 2

Treatment of Individuals with Asperger's Disorders with Oxytocin and A Psychopharmacologic Agent Benefits may be reaped by co-administering oxytocin and a psychopharmacologic agent to patients diagnosed with Asperger's disorder. Oxytocin and the psychopharmacologic agent may be administered in the same infusion mixture. The initial vial of Pitocin® (10 u/mL) and/or valium (10 u/mL) can be combined aseptically with a 1.0 L bag of normal saline and administered at a rate of 10 mL/hr. The infusion can be initiated at a low rate to minimize potential side effects, and the rate gradually titrated up. Specifically, the infusion rate can be titrated every 15 minutes by 25 mL in the first hour, 50 mL in the second hour, 100 mL in the third hour, and then held constant at the maximum rate of 700 mL/hr during the fourth hour. The combined solution, rotated in an infusion bottle to insure thorough mixing, can be added to the system by a constant infusion pump to accurately control the rate of infusion.

An additional therapeutic agent may be co-administered with the Pitocin® or administered at a later time to be determined by the physician. The interval between administration of Pitocin® and the additional agent may range from minutes to hours or from days to weeks, depending on the optimum therapeutic dosing schedule.

Example 3

Treatment of Individuals with Attention Deficiency Disorder (ADD) with Oxytocin

Individuals with attention deficiency disorder (ADD) can be treated with Oxytocin and or Oxytocin analogs either alone or in combination with another agent as described in Examples 1 and 2.

Example 4

Treatment of Individuals with a Disorder Associated with a Repetitive Behavior, a Social Deficit and/or a Cognitive Deficit with Oxytocin Individuals with disorders associated with a repetitive behavior, a social deficit and/or a cognitive deficit can be treated with Oxytocin and/or Oxytocin analogs either alone or in combination with another agent as described in Examples 1 and 2.

All of the methods disclosed and claimed herein can be made and executed without undue experimentation in light of the present disclosure. While the compositions and methods of this invention have been described in terms of preferred embodiments, it will be apparent to those of skill in the art that variations may be applied to the compositions, and methods and in the steps or in the sequence of steps of the methods described herein without departing from the concept, spirit and scope of the invention. More specifically, it will be apparent that certain agents that are both chemically and physiologically related may be substituted for the agents described herein while the same or similar results would be achieved. All such similar substitutes and modifications apparent to those skilled in the art are deemed to be within the spirit, scope, and concept of the invention as defined by the appended claims.

I claim:

1. In a method for treatment of an individual with autism, by administration of a psychopharmacologic agent, the improvement comprising:
   additional administration of a therapeutically effective amount of a composition comprising oxytocin having the formula,

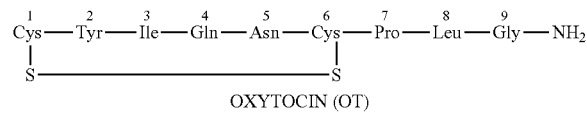

OXYTOCIN (OT)

wherein the psychopharmacologic agent is selected from the group consisting of sedatives, tranquilizers, antipsychotics, antidepressants, and anticonvulsants; and
   wherein the psychopharmacologic agent and the additional composition are administered within about 6-24 hours of each other.

2. The method of claim 1, wherein said therapeutically effective amount ranges from 0.1 unit per hour to 7 units per hour.

3. In a method for treatment of an individual with an autism spectrum disorder by administration of a psychopharmacologic agent, the improvement comprising:
   additional administration of a therapeutically effective amount of a composition, comprising oxytocin having the formula,

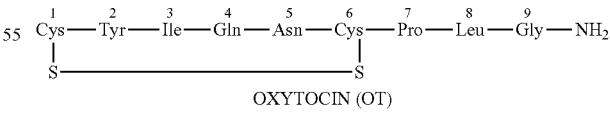

OXYTOCIN (OT)

wherein the psychopharmacologic agent is selected from the group consisting of sedatives, tranquilizers, antipsychotics, antidepressants, and anticonvulsants; and
   wherein the psychopharmacologic agent and the additional composition are administered within about 6-24 hours of each other.

4. The method of claim 3, wherein said therapeutically effective amount is 10 units per ml oxytocin dissolved into 1000 mL normal saline, administered at a rate of 10 milliunits per minute or 6 units/hour.

\* \* \* \* \*